(12) United States Patent
Deppermann et al.

(10) Patent No.: US 7,909,276 B2
(45) Date of Patent: Mar. 22, 2011

(54) AGRICULTURAL SAMPLE GRINDER

(75) Inventors: Kevin Deppermann, St. Charles, MO (US); Angela Koestel, St. Louis, MO (US); Tavis Aholt, Washington, MO (US)

(73) Assignee: Monsanto Technology LLC, St. Louis, MO (US)

( * ) Notice: Subject to any disclaimer, the term of this patent is extended or adjusted under 35 U.S.C. 154(b) by 334 days.

(21) Appl. No.: 12/032,138

(22) Filed: Feb. 15, 2008

(65) Prior Publication Data

US 2008/0203201 A1 Aug. 28, 2008

Related U.S. Application Data

(60) Provisional application No. 60/891,419, filed on Feb. 23, 2007.

(51) Int. Cl.
*B02C 23/20* (2006.01)
(52) U.S. Cl. ..... 241/60; 241/100; 241/282.1; 241/282.2
(58) Field of Classification Search .................. 241/100, 241/60, 282.1, 282.2
See application file for complete search history.

(56) References Cited

U.S. PATENT DOCUMENTS

| 3,685,748 | A | | 8/1972 | Beck et al. |
| 3,958,765 | A | * | 5/1976 | Musselman ..................... 241/99 |
| 3,987,970 | A | | 10/1976 | Burkett |
| 4,778,117 | A | | 10/1988 | Karg |
| 4,971,261 | A | * | 11/1990 | Solomons ..................... 241/99 |
| 5,082,188 | A | | 1/1992 | Urich |
| 5,201,474 | A | * | 4/1993 | Midden ....................... 241/100 |
| 5,417,376 | A | | 5/1995 | Holmes et al. |
| 5,660,339 | A | * | 8/1997 | Scott et al. ..................... 241/60 |
| 5,743,473 | A | * | 4/1998 | Gregg ........................... 241/33 |
| 2004/0056128 | A1 | | 3/2004 | Uebayashi et al. |
| 2004/0069880 | A1 | * | 4/2004 | Samelson et al. ............... 241/74 |

FOREIGN PATENT DOCUMENTS

| DE | 29721670 U1 | 12/1997 |
| EP | 1484114 A1 | 12/2004 |
| GB | 2310213 | 8/1997 |
| JP | 03046537 | 2/1991 |
| JP | 08229421 | 9/1996 |
| JP | 11030612 | 2/1999 |
| WO | WO 83/01913 | 6/1983 |

* cited by examiner

*Primary Examiner* — Bena Miller
(74) *Attorney, Agent, or Firm* — James E. Davis; Joseph A. Schaper; Harness, Dickey & Pierce, P.L.C.

(57) ABSTRACT

In various embodiments, an agricultural sample grinding system is provided. The system includes a grinder unit for grinding and uniformly mixing an agricultural sample. The system additionally includes a collection chamber connected to a transfer spout extending from a side of the grinder unit. The collection chamber is for collecting the ground and uniformly mixed agricultural sample dispensed from the grinder unit via the transfer spout. The system deposits the ground and uniformly mixed agricultural sample into the collection chamber such that the uniform mixture of the sample is maintained.

25 Claims, 9 Drawing Sheets

AGRICULTURAL SAMPLE GRINDER

CROSS-REFERENCE TO RELATED APPLICATIONS

This application claims the benefit of U.S. Provisional Application No. 60/891,419, filed on Feb. 23, 2007. The disclosure of the above application is incorporated herein by reference in its entirety.

FIELD OF INVENTION

The invention relates generally to systems and methods for grinding and uniformly mixing agricultural samples.

BACKGROUND OF THE INVENTION

Agricultural development companies and other businesses within the agricultural industry often analyze samples of agricultural products, such as seeds and plant tissue, to determine various traits or characteristics of the sample. For example, in seed breeding, large numbers of seeds are sampled and analyzed to determine whether the seeds possess traits of interest. Often, to analyze a sample of an agricultural product, the sample is ground into very small particulates and mixed. Various testing can then be performed on the mixed sample to determine various traits or characteristics. For example, the mixed sample can undergo near infrared (NIR) testing to determine certain organic chemical levels of the sample.

Accurate testing of ground samples requires that the sample be uniformly mixed and that the uniform mixture be maintained during testing. However, known seed grinding systems and methods generally fail to produce sufficiently uniform mixtures resulting in undesirable striations in the sample leading to non-representative samples for testing. Additionally, known grinding systems and methods typically are not capable of automatically transferring the ground and mixed sample to the desirable sample container to be used during analysis.

BRIEF SUMMARY OF THE INVENTION

In various embodiments, an agricultural sample grinding system is provided. The system includes a grinder unit for grinding and uniformly mixing an agricultural sample. The system additionally includes a collection chamber connected to a transfer spout extending from a side of the grinder unit. The collection chamber is for collecting the ground and uniformly mixed agricultural sample dispensed from the grinder unit via the transfer spout. The system deposits the ground and uniformly mixed agricultural sample into the collection chamber such that the uniform mixture of the sample is maintained.

In various other embodiments, an agricultural sample grinding system is provided. The system includes a grinder unit having a grinding chamber for grinding and uniformly mixing an agricultural sample. The system additionally includes a collection chamber connected to the grinder unit for collecting ground and uniformly mixed agricultural sample dispensed from the grinder unit. The system further includes an automatic transfer control assembly for transferring the ground and uniformly mixed sample from the grinding chamber to the collection chamber. The system deposits the ground and uniformly mixed agricultural sample into the collection chamber while maintaining the uniform mixture of the sample.

In yet other various embodiments, a method for grinding, mixing and collecting a uniformly mixed agricultural sample is provided. The method includes grinding and uniformly mixing an agricultural sample utilizing a rotary blade within a grinding chamber of a grinder unit. Rotation of the blade causes the ground and uniformly mixed sample to spin and exert centrifugal force within the grinding chamber. The method additionally includes utilizing the centrifugal force of the spinning ground and uniformly mixed sample to transfer the ground and uniformly mixed sample from the grinding chamber to a collection chamber. The spinning ground and uniformly mixed sample is transferred via an outflow port extending from the grinding chamber through a side of the grinder unit. Transferring the ground and uniformly mixed sample while the ground and uniformly mixed sample is spinning allows the uniformity of the mixture to be maintained. The method further includes collecting and retaining the ground and uniformly mixed sample substantially free of striations in a sample receptacle cooperatively mated with the collection chamber.

Further areas of applicability of the present invention will become apparent from the detailed description provided hereinafter. It should be understood that the detailed description and specific examples, while indicating the preferred embodiments of the invention, are intended for purposes of illustration only and are not intended to limit the scope of the invention. Furthermore, the features, functions, and advantages of the present invention can be achieved independently in various embodiments of the present inventions or may be combined in yet other embodiments.

BRIEF DESCRIPTION OF THE DRAWINGS

The present invention will become more fully understood from the detailed description and accompanying drawings, wherein.

Corresponding reference numerals indicate corresponding parts throughout the several views of drawings.

DETAILED DESCRIPTION OF THE INVENTION

The following description of the preferred embodiments is merely exemplary in nature and is in no way intended to limit the invention, its application or uses. Additionally, the advantages provided by the preferred embodiments, as described below, are exemplary in nature and not all preferred embodiments provide the same advantages or the same degree of advantages.

Figure 1:
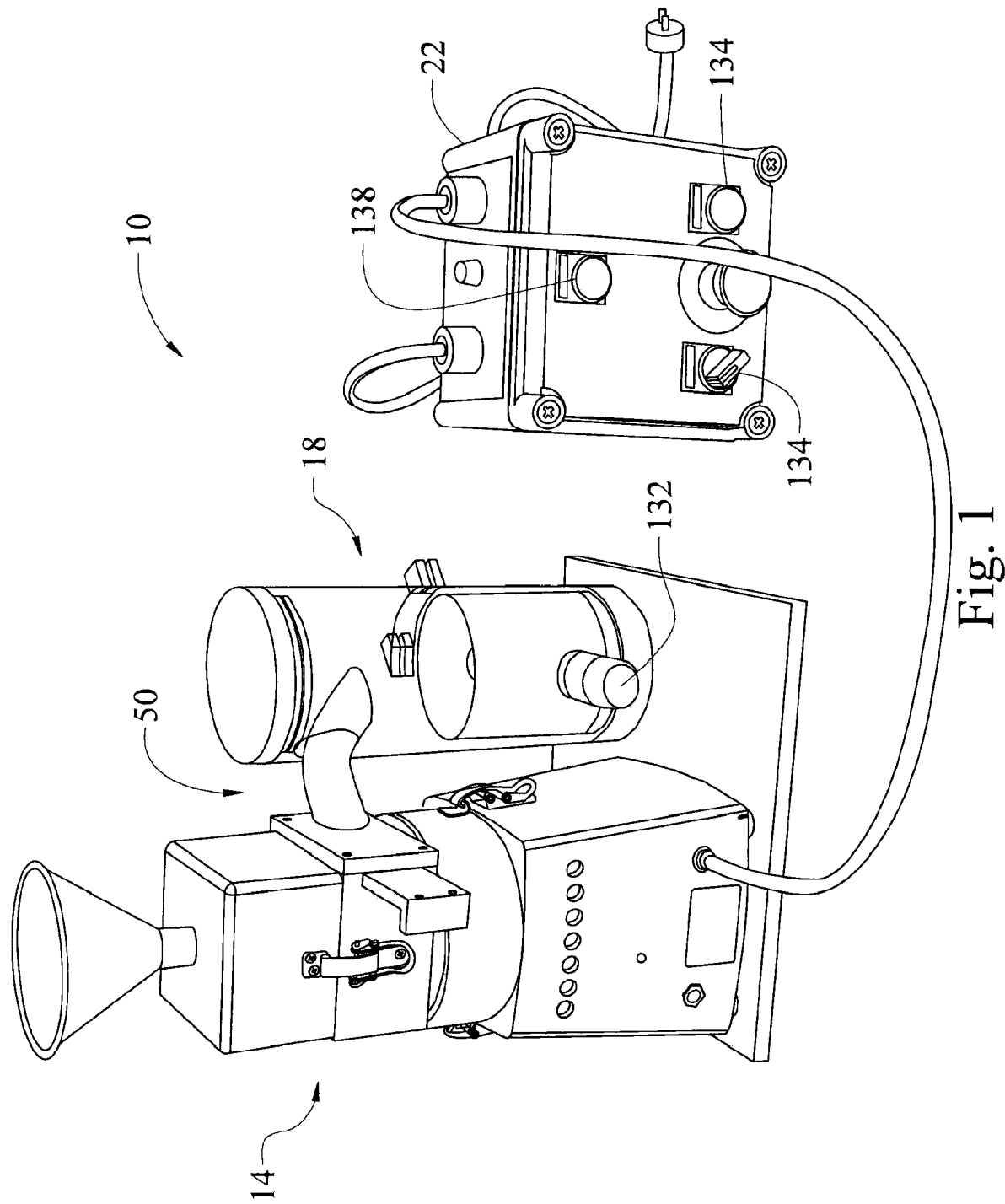
FIG. 1 is an isometric view of an agricultural sample grinding system, in accordance with various embodiments of the present disclosure.

Referring to FIG. 1, an agricultural sample grinding system 10 is provided. The grinding system 10 is utilized for grinding samples of agricultural products, such as seeds and plant tissue, to be analyzed for determination of various traits and/or characteristics of the sample. For example, various samples of seeds can be ground and analyzed to determine whether the particular seed sample possesses certain chemical characteristics, genetic characteristics and/or other traits of interest. More particularly, the grinding system 10 grinds the selected sample into very small particulates, mixes the particulates to achieve a substantially uniform mixture and transfers the mixture to a sample cup while maintaining its uniformity. The ground and uniformly mixed sample can then undergo various testing to determine the various traits and/or characteristics of the sample. For example, the uniformly mixed sample can undergo near infrared (NIR) or various other types of testing to determine certain organic content levels of the sample, such as oil, protein, starch and/or moisture levels, or provide DNA, protein and/or amino acids analysis.

The grinding system 10 generally includes a grinding and mixing assembly (GMA) 14 for grinding and uniformly mixing an agricultural sample, and a collection chamber 18 for collecting the ground and uniformly mixed sample that is automatically transferred from the GMA 14. In various embodiments, the grinding system 10 can additionally include a control unit 22 communicatively coupled with GMA 14 for controlling operation of the GMA 14. The control unit 22 can be communicatively coupled with the GMA 14 via a hard wired connection, as illustrated in FIG. 1, or a wireless connection, e.g., infrared signals or radio frequency (RF) signals.

Figure 2:
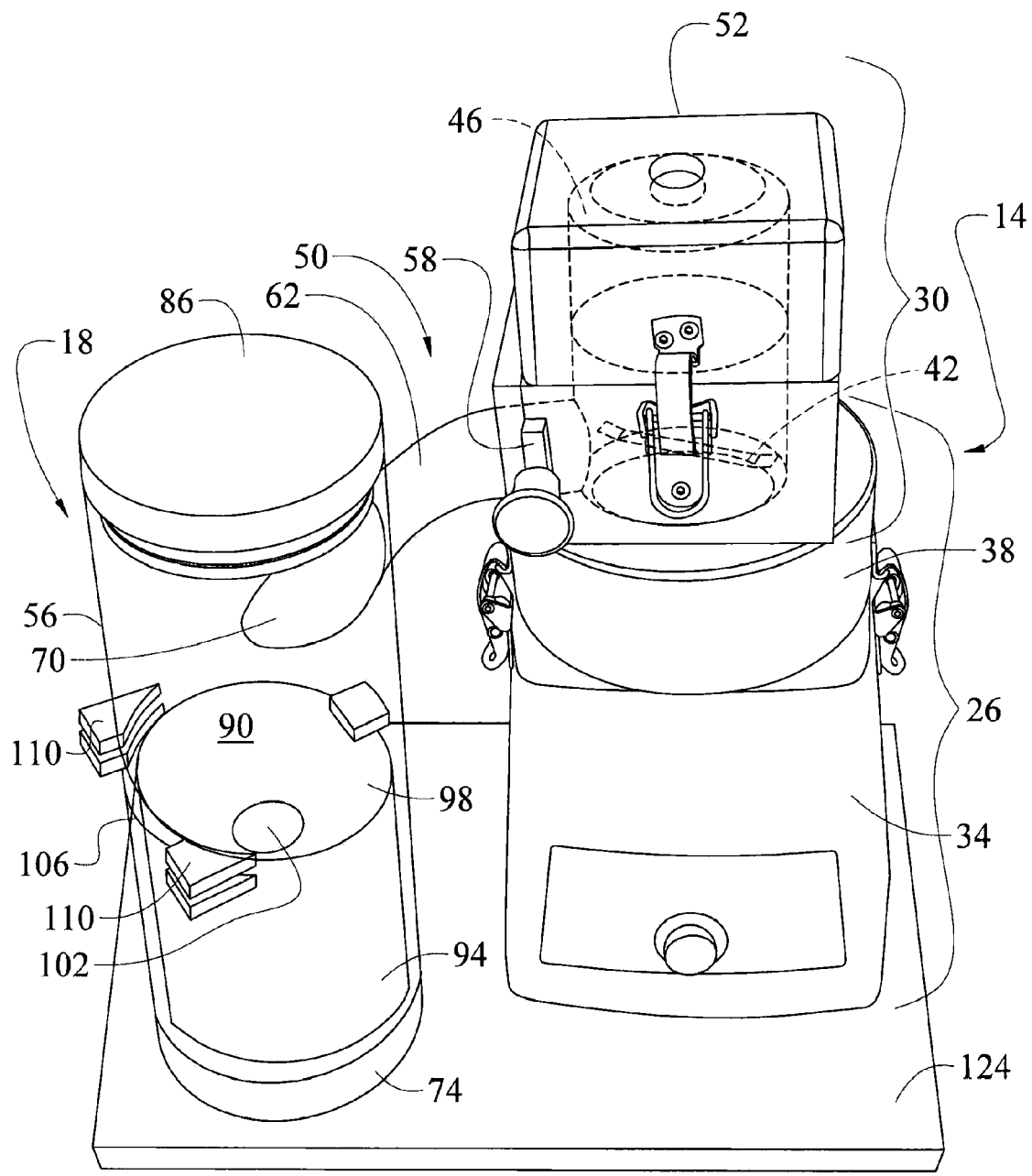
FIG. 2 is an isometric view of a grinding mixing assembly connected with a collection chamber via an automatic transfer control assembly of the agricultural sample grinding system shown in FIG. 1, in accordance with various embodiments of the present disclosure.

Referring now to FIG. 2, in various embodiments, the GMA 14 includes a drive train subassembly 26 that is mechanically coupled to a grinder unit 30. The drive train subassembly 26 includes a motor (not shown), enclosed within a motor housing 34, that drives a transmission (not shown) enclosed within a transmission housing 38. The motor can by any suitable motor rated to provide torque, RPMs and power sufficient to grind the sample, uniformly mix the sample and create centrifugal force within the sample suitable for transferring the sample to the collection chamber 18, as described further below. For example, in various embodiments, the motor can be an off-the-shelf motor having torque, RPM and power ratings desirable for laboratory grinding. The transmission is mechanically coupled to a grinding blade 42 within the grinder unit 30 and provides torque to rotate the grinding blade 42 within a grinding chamber 46, as described further below. The grinding system 10 additionally includes an automatic transfer control assembly (ATCA) 50 that connects the grinder unit 30 with the collections chamber 18. More particularly, the ATCA 50 provides a means for transferring the ground and uniformly mixed sample for the grinding chamber 46 to the collection chamber 18 while maintaining the uniform mixture of the sample.

Figure 3:
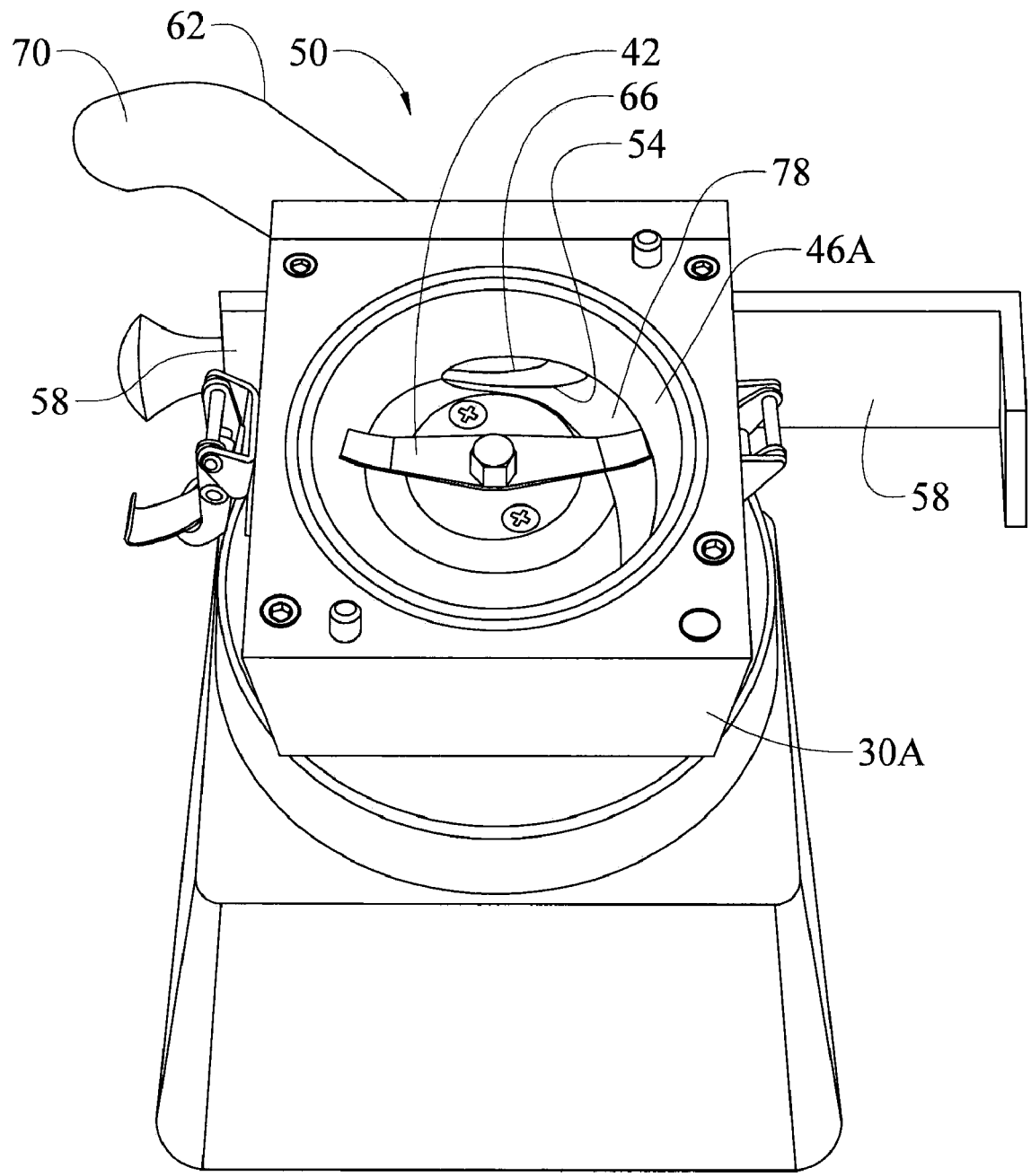
FIG. 3 is an isometric view of a grinding chamber of the grinding and mixing assembly, in accordance with various embodiments of the present disclosure.
Figure 4:
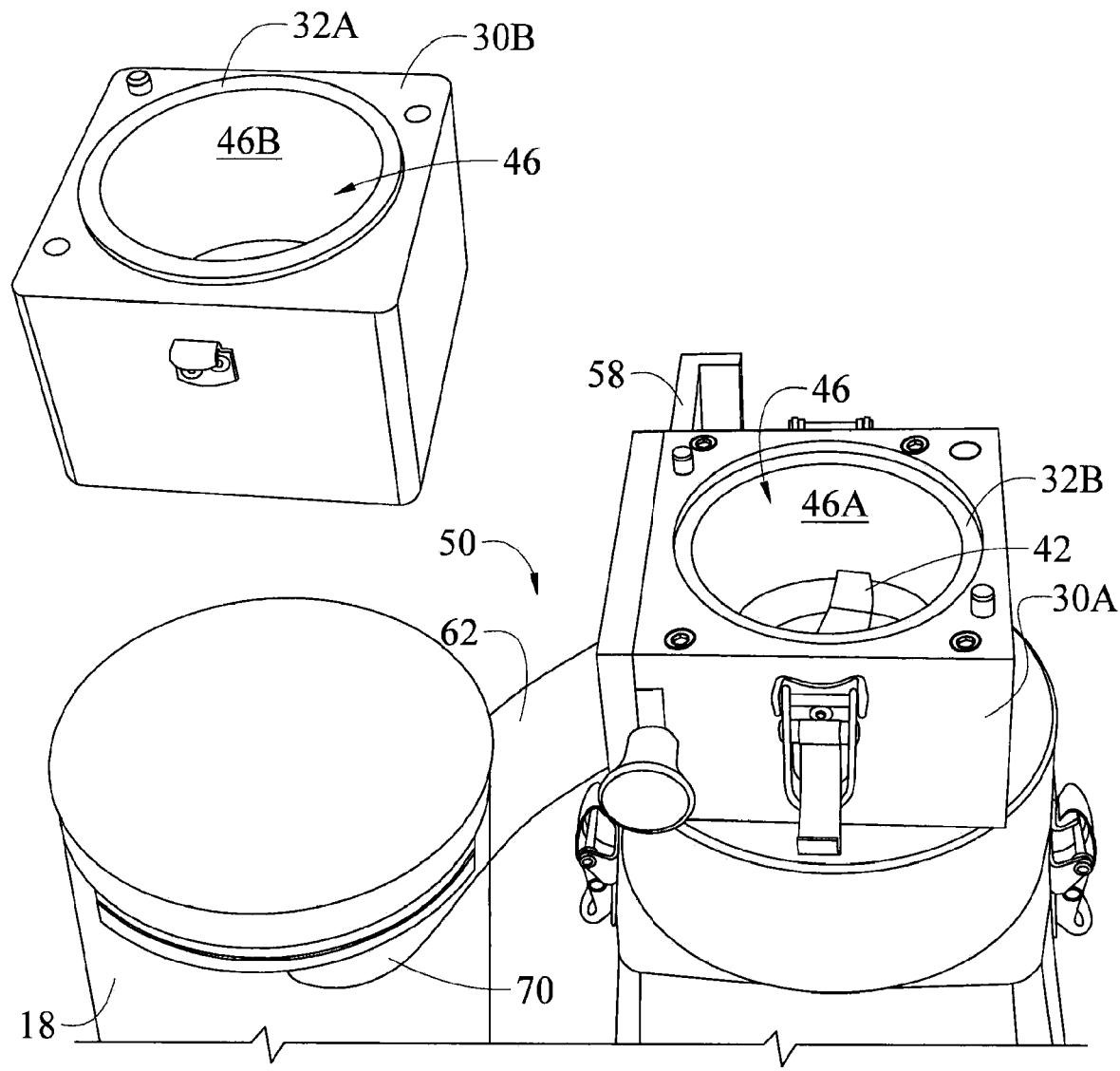
FIG. 4 is an isometric view of a portion of the agricultural sample grinding system illustrating the automatic transfer control assembly, in accordance with various embodiments.

Referring now to FIGS. 3 and 4, as described above, the grinder unit 30 includes a grinding chamber 46 formed within an interior of the grinder unit 30. More particularly, the grinding unit 30 includes a bottom half 30A and a top half 30B that respectively include a grinding chamber bottom half 46A and a grinding chamber top half 46B. As exemplarily illustrated in FIG. 4, in various embodiments, one of the grinder unit bottom or top halves 30A or 30B includes an annular raised ridge 32A formed around a perimeter of the respective bottom or top half 46A or 46B of the grinding chamber 46. The annular raised ridge 32A mates with an annular channel 32B formed around a perimeter of the respective opposing bottom or top half 46A or 46B of the grinding chamber 46. Therefore, when the grinder unit bottom and top halves 30A and 30B are coupled together, the raised ridge and channel 32A and 32B mate to precisely align the bottom and top halves 46A and 46B of the grinding chamber. Thus, the overall surface of the grinding chamber 46, as a whole, is smooth and substantially without cracks, crevices or gaps.

The grinding blade 42 is coupled to the grinding and mixing assembly transmission and rotationally mounted within the grinding chamber bottom half 46A. Thus, operation of the grinding and mixing assembly motor will cause the grinding blade 42 to spin, i.e., rotate within the grinding chamber bottom half 46A, thereby grinding and mixing any agricultural sample that has been deposited in the grinding chamber 46. In various embodiments, the top half 30B of the grinding unit 30 is detachably connected to the bottom half 30A using any suitable latching means, such as a pair of spring clasp, screws, snaps, buckles, pins, etc. Therefore, the grinding unit top half 30B can be removed and the bottom and top halves 46A and 46B of the grinding chamber 46 can be easily cleaned to remove any remaining particulate matter. Additionally, a surface of the grinding chamber 46 is constructed to provide a very smooth surface that will allow for any remaining particulate matter to be easily removed from the grinding chamber 46 to prevent contamination of a subsequently ground and mixed sample. For example, in various embodiments, the grinding chamber surface is hardened and polished to make it smooth, durable and easy to clean, for example the grinding chamber surface can be anodized aluminum.

In various embodiments, the grinding chamber top half 30B includes a sample deposit port 52 (best shown in FIG. 2) for depositing a sample into the grinding chamber when the top half 30B is coupled to the bottom half 30A. For example, a funnel can be inserted into the sample deposit port 52, as shown in FIG. 1, into which a desired agricultural sample can be poured. Accordingly, the desired sample can be deposited into the grinding chamber where it will be ground, mixed and automatically transferred to the collection chamber while remaining uniformly mixed.

Furthermore, in various embodiments, the size, shape and contour of the grinding chamber 46, i.e., both the bottom and top halves 46A and 46B, are formed to optimize grinding and mixing the sample to a desired particulate size, uniformity of size and homogeneity. Also, as described further below, the grinding system 10 includes a timer that controls the length of time the grinding blade spins to assist in optimization of the grinding and mixing. Additionally, the size, shape and contour of the grinding chamber 46 are designed to maximize the amount of ground and mixed sample that is transferred to the collection chamber. For example, in various embodiments, a bottom portion of the surface of the grinding chamber bottom half 46A, and a top portion of the surface of the grinding chamber top half 46B each have a curved or rounded perimeter region that forms a bowl-like shape. To accommodate the bowl-like shape of the grinding chamber bottom surface and increase the efficiency of the grinding, mixing and transferring of the sample, tips of the grinding blade 42 are upwardly bent or curved toward the grinding chamber top half 43B. The automatic transfer of the ground and uniformly mixed sample from the grinding chamber 46 to the collection chamber 18 is described further below.

Referring now to FIGS. 2, 3 and 4, the ATCS 50 includes an outflow port 54, a flow control gate 58 and a transfer spout 62. The outflow port 54 extends from the grinding chamber bottom half 46A through a sidewall of the grinder unit bottom half 30A. The flow control gate 58 is cooperative with an exterior side of the bottom half 30A of the grinder unit 30 to control dispensing of the ground and uniformly mixed sample from the grinding chamber 46. Specifically, the flow control gate 58 is cooperative with the exterior side of the grinding unit bottom half 30A such that it is moveable between an 'Open' position and a 'Closed' position. More particularly, the flow control gate 58 includes an aperture 66 that is alignable with the control gate aperture 66 by positioning the flow control gate in the Open position. In various embodiments, the flow control gate 58 is slidingly attached to the exterior side of the grinding unit bottom half 30A such that the flow control gate can be slidingly transitioned between the Open and Closed positions. The transfer spout 62 comprises a tubular structure that is coupled at a proximal end to the same exterior side of the grinder unit bottom half 30A as the transfer control gate 58. The transfer spout 62 is coupled to the grinder unit bottom half 30A such that an internal bore of the transfer spout 62 aligns with outflow port 54 having the flow control gate 58 positioned therebetween. A distal end portion 70 of the transfer spout 62 extends through a sidewall 56 of the collection chamber 18. The distal end portion 70 is curved or bent such that the internal bore opening at a distal end of the transfer spout 62 is directed downward generally toward a center of a bottom of the collection chamber 18.

A routing channel 78 is formed in the bottom portion of the surface of the grinding chamber bottom half 46A. The routing channel 78 provides a guide for the ground and mixed sample that is spinning within the grinding chamber, due to the rotation of the grinding blade 42, to be dispensed through the outflow port when the flow control gate is moved to the open position. Particularly, when the flow control gate is opened, centrifugal force created within the spinning ground and uniformly mixed sample causes the sample to be expelled from the grinding chamber, through the outflow port 54, the flow control gate aperture 66 and the internal bore of transfer spout 62, into the collection chamber 18. Furthermore, the expelled, or dispensed, ground and uniformly mixed sample is deposited into a sample receptacle 82, described below and exemplarily illustrated in FIG. 5.

Figure 5:
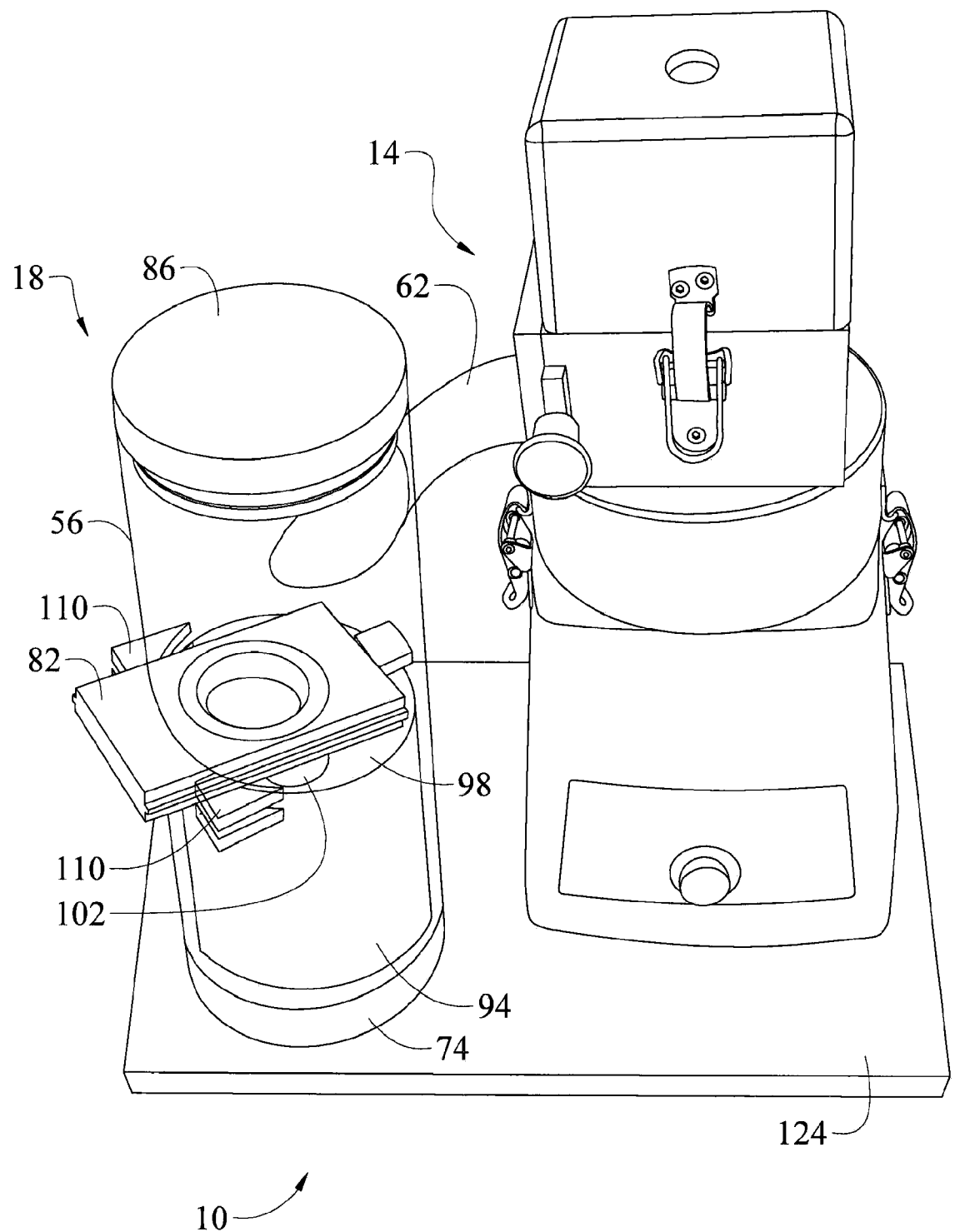
FIG. 5 is an isometric view of the agricultural sample grinding system shown in FIG. 1 illustrating a sample receptacle installed within the collection chamber, in accordance with various embodiments of the present disclosure.
Figure 6:
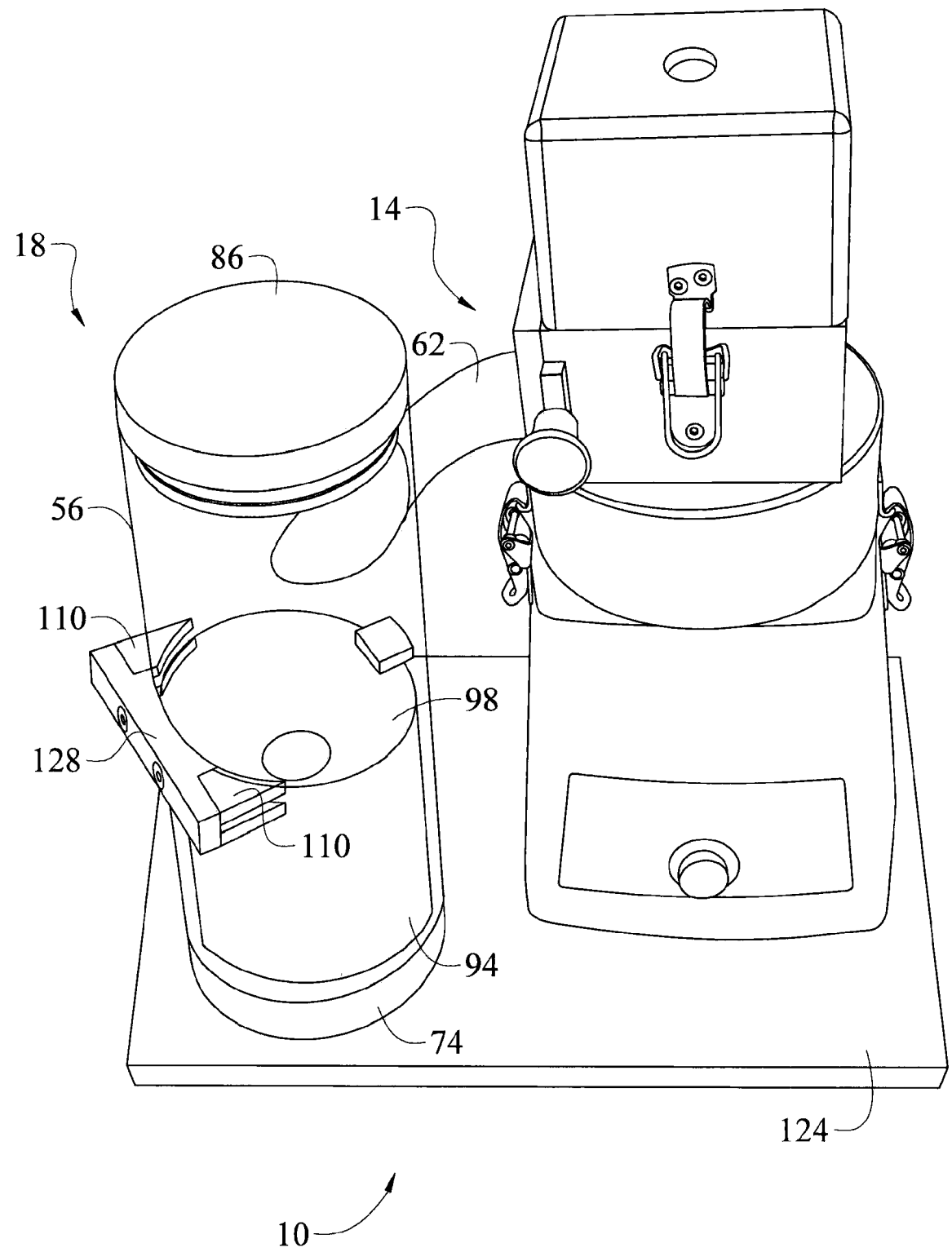
FIG. 6 is an isometric view of the agricultural sample grinding system shown in FIG. 1 illustrating a sample receptacle port block installed within the collection chamber, in accordance with various embodiments of the present disclosure.

Referring now to FIGS. 2, 5 and 6, in various embodiments the collection chamber 18 is a cylindrical chamber including the sidewall 56, the bottom 74 attached to the sidewall 56 and a removable lid 86. The cylindrical shape eliminates corners where ground sample particulates can gather and possibly contaminate subsequent samples collected within the collection chamber 18. The cylindrical shape also aids in the ease of cleaning the collection chamber to remove residual ground sample particulates. The collection chamber 18 additionally includes a sample funnel 90 positioned within a lower portion of the collection chamber 18. An outer surface 94 of the sample funnel 90 is effectively sealed against an interior of the collection chamber sidewall 56. Therefore, ground sample particulates cannot fall along the sides of the funnel 90 where they would be difficult to remove. Rather, the ground sample particulates slide down along a concave top surface 98 of the funnel 90 and fall into a bottom opening 102 of the funnel 90.

The collection chamber 18 further includes a sample receptacle slot 106 that extends through the collection chamber sidewall 56, shown in FIG. 2. The sample receptacle slot 106 is adapted to receive various different sample receptacles 82 that are inserted through the collection chamber sidewall 56, via the sample receptacle slot 106. Accordingly, a sample receptacle 82, such as the exemplary sample receptacle 82 shown in FIG. 5, can be positioned within the interior of the collection chamber 18. The collection chamber 18 further includes one or more sample receptacle guides 110 located adjacent one or more ends of the sample receptacle slot 106. The sample receptacle guide(s) 110 are utilized to guide the sample receptacle 82 as it is inserted through the sample receptacle slot, thereby positioning the sample receptacle 82 properly within the collection chamber 18. Specifically, the sample receptacle guide(s) 110 assist in positioning a removable collection cup 114 of the sample receptacle 82 under the distal end of the transfer spout 62. Therefore, when the ground and uniformly mixed sample is dispensed from the grinding chamber 46, it travels through the transfer spout 62 and is deposited into the collection cup 114, while maintaining the uniform mixture of sample.

Figure 7:
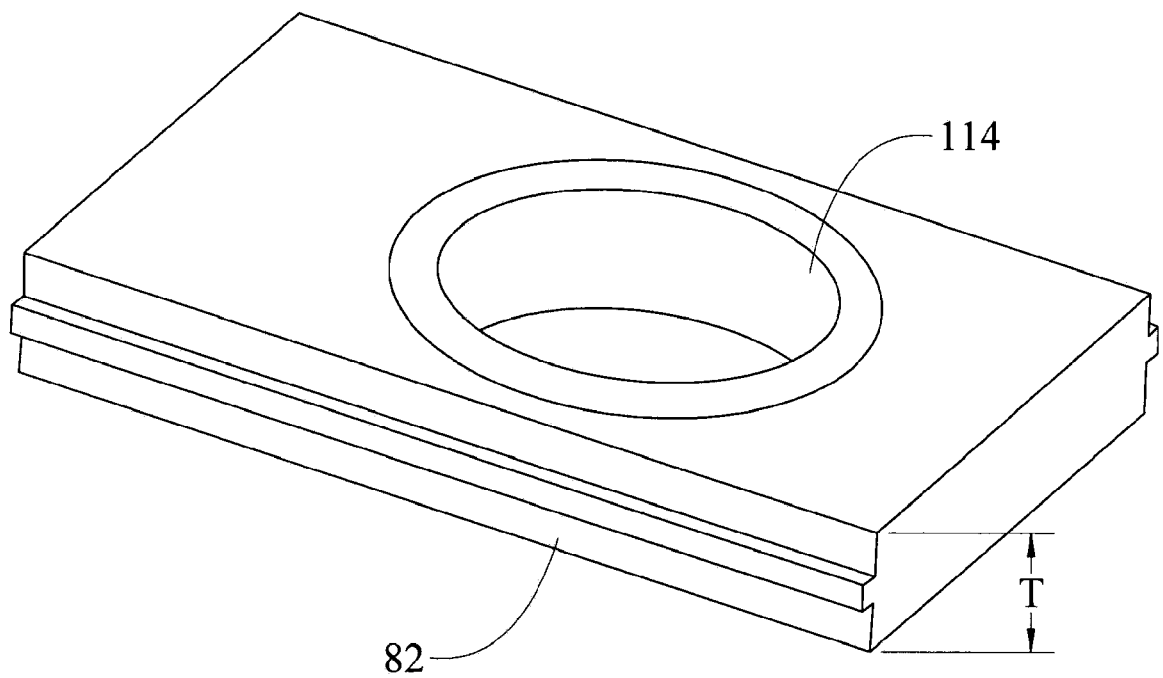
FIG. 7 is an isometric view of a sample receptacle included in the agricultural sample grinding system shown in FIG. 1, in accordance with various embodiments of the present disclosure.
Figure 8:
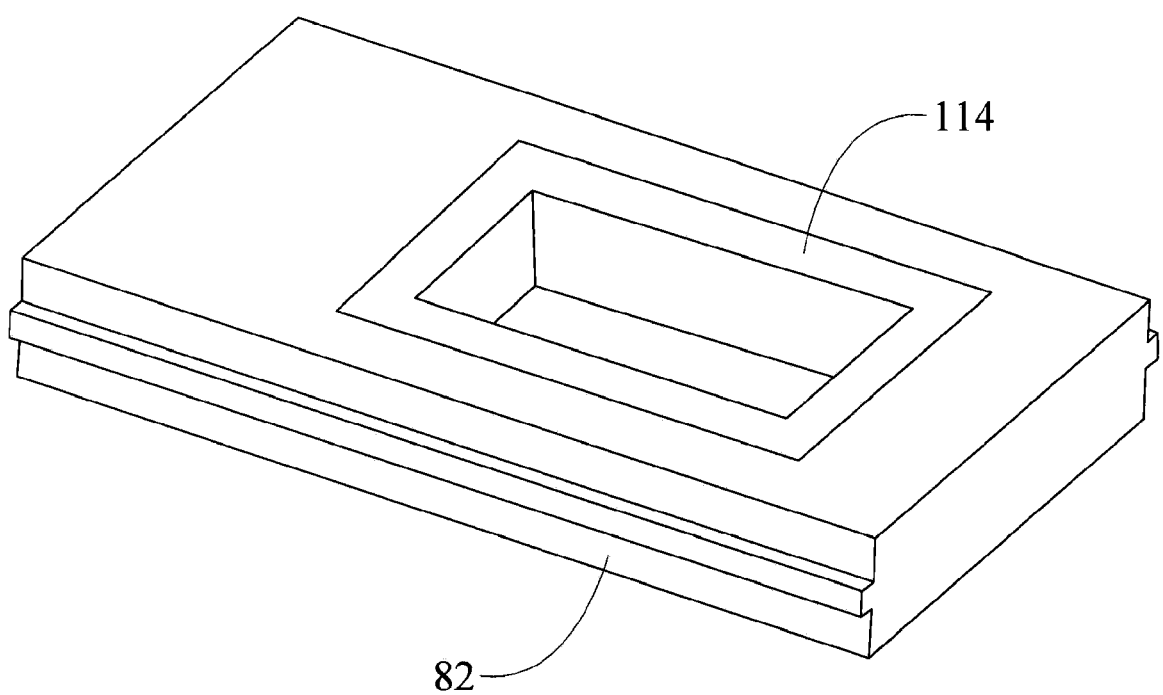
FIG. 8 is an isometric view of a sample receptacle included in the agricultural sample grinding system shown in FIG. 1, in accordance with various other embodiments of the present disclosure.

Referring to FIGS. 7 and 8, the sample receptacle 82 can removably retain any desirable size and/or shape of collection cup 114. For example, as illustrated in FIG. 7, in various embodiments the collection cup 114 can have a round shape, while in other embodiments, the collection cup 114 can have a rectangular shape, as illustrated in FIG. 8. The exemplary embodiments shown in FIGS. 7 and 8 should not be considered limiting. It should be understood that in various other embodiments the collection cup 114 can have any other desirable shape, for example, oval, square, hexagonal, octagonal, etc. Furthermore, the collection cup 114 can have a depth that is approximately equal to, less than or greater than a thickness T of the collection receptacle 82.

Figure 9:
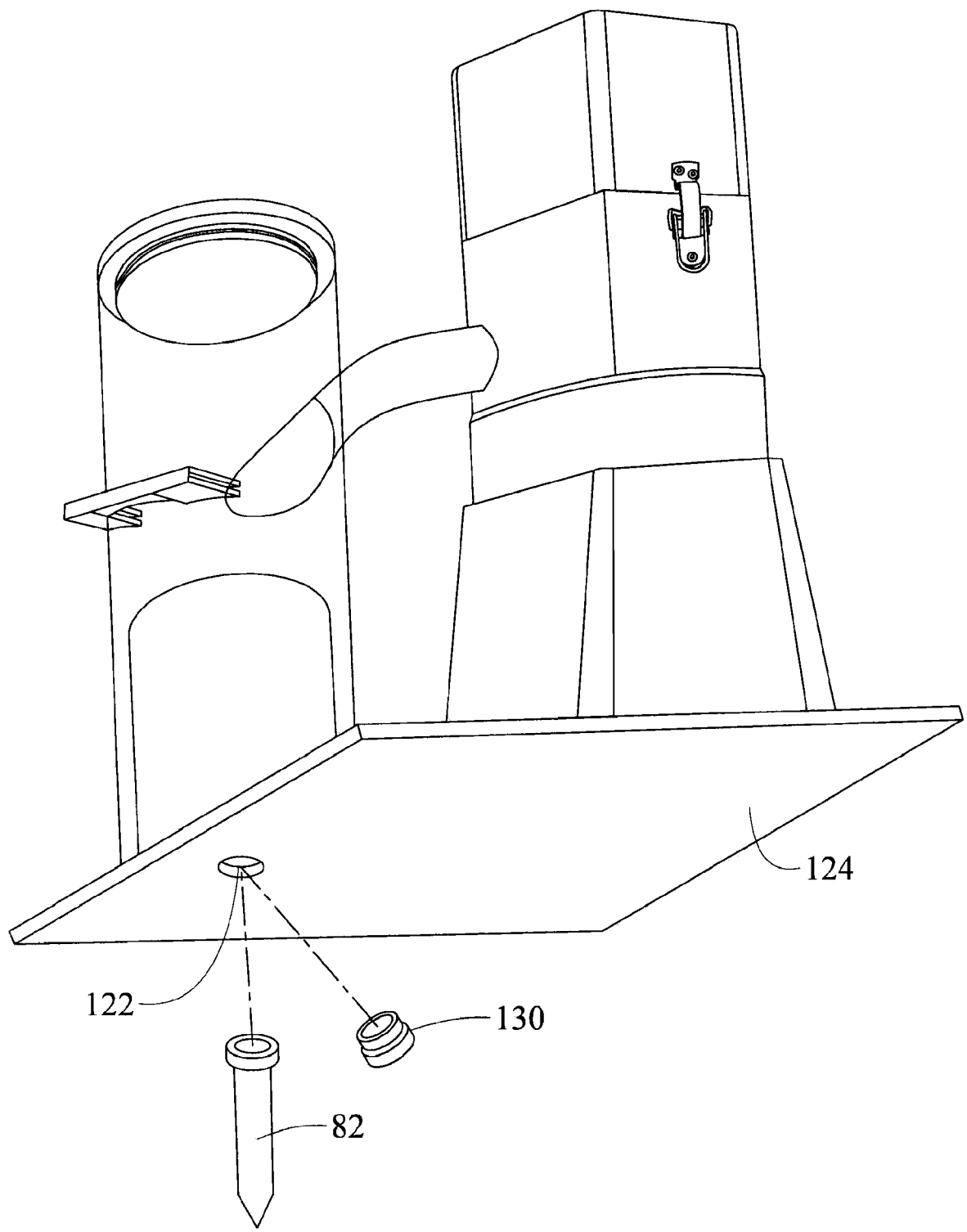
FIG. 9 is an isometric view of the agricultural sample grinding system shown in FIG. 1, illustrating a bottom port of the collection chamber and a tubular collection receptacle that is removably attachable to the bottom port, in accordance with various embodiments of the present disclosure.

Referring now to FIGS. 6 and 9, in various embodiments, the agricultural sample grinding system 10 includes a bottom port 122 that extends through a base 124 of the grinding system 10 and through the bottom 74 of the collection chamber 18. Specifically, the bottom port 122 aligns with the funnel opening 102 of the collection chamber sample funnel 90. In such embodiments, the sample receptacle 82 can have the form of a conical tube that is removably connectable to the system base 124 at the bottom port 122. Thus, the ground and uniformly mixed sample can be dispensed from the grinding chamber 46, as described above, and deposited into the collection chamber funnel 90. The ground and uniformly mixed sample can then fall through the funnel opening 102 into a collection receptacle 82 removably attached to the system base 124 and bottom port 122. Additionally, in such embodiments, a sample receptacle slot block 128 can be inserted into the sample receptacle slot 106 in the sidewall 56 of the collection chamber 18. The slot block 128 blocks any ground and uniformly mixed sample from escaping out the sample receptacle slot 106 when a sample receptacle 82 is not inserted therein. Conversely, when a collection receptacle 82 is not coupled to the system base 124, a bottom port plug 130 can be inserted into the bottom port 122.

In various other embodiments, a sample receptacle 82 can be inserted into the sample receptacle slot 106 to collect the ground and uniformly mixed sample in a collection cup 114, and the bottom port 122 can be left open, i.e., without a conical collection receptacle 82 coupled thereto or the bottom port plug 130 in place. In this configuration, any excess ground and mixed sample that is not collected in the collection cup 114 can fall through the sample funnel 90 and out the bottom port into a waste collection container (not shown).

Referring to FIG. 1, in various embodiments, the agricultural sample grinding system 10 additionally includes a vacuum port 132. The vacuum port 132 extends through the collection chamber sidewall 56 and through an outer wall of the funnel 90, where the vacuum port 132 joins with the funnel opening 102. A vacuum source (not shown), such as a common workshop vacuum machine, can be connected to the vacuum port 132 to remove, i.e., vacuum out, any residual ground sample particulates that may remain within the collection chamber 18, transfer spout 62 and/or grinding chamber 46 after a particular sample has been ground, dispensed, collected and removed from the collection chamber 18.

Accordingly, to grind and collect a uniformly mixed agricultural sample, the desired sample to be analyzed is deposited into the grinding chamber 46, via the sample deposit port 52. The motor is then commanded to rotationally drive the grinding blade 42 for a predetermined amount of time. In various embodiments, operation of the motor can be controlled by the control unit 22, shown in FIG. 1. The control unit 22 includes various timers and switches 134 that can be set to control the length of time the motor turns the grinding blade 42 and/or the torque and/or the speed at which the motor turns the grinding blade 42. Additionally, in various embodiments, the control unit 22 can include a timer 138 that can be utilized to indicate when a predetermined time has elapsed, after grinding of the sample has begun, at which the sample is properly ground to the desired particulate size. The ATCA 50 can them be operated to dispense the ground and uniformly mixed sample into the collection chamber.

As the grinding blade 42 spins to grind the agricultural sample, the spinning blade 42 imparts force on the grinding sample and causes the grinding and mixing sample to rotate or spin within the grinding chamber 46. Thus, the spinning sample generates a centrifugal force causing the ground particulates to push radially outward against the side, top and bottom of the grinding chamber 46. Once the sample has been adequately ground and mixed, the flow control gate 58 can be operated, either manually or automatically, to align the flow control gate aperture 66 with the ATCA outflow port 54. As the flow control gate aperture 66 aligns with the ATCA outflow port 54 the centrifugal force carried by the spinning ground and uniformly mixed particulates causes the ground and uniformly mixed sample to flow through the ATCA outflow port 54. The spinning ground and uniformly mixed sample is thereby dispensed into the collection chamber 18 and collected in the sample receptacle 82, or collection cup 114, as described above. More specifically, the spinning ground and uniformly mixed sample is dispensed into the sample receptacle 82, or collection cup 114, without letting the ground and mixed sample settle within the grinding chamber 46. By depositing the ground and uniformly mixed sample into the sample receptacle 82, or collection cup 114, without letting the ground and mixed sample to settle within the grinding chamber 46, the uniform mixture of the sample is maintained.

Put another way, by moving the transfer gate 58 to the open position while the sample is still spinning, the sample is transferred to the collection cup 114 while the sample is still mixing. That is, the sample is not allowed to stop mixing and come to rest before being transferred to the collection cup 114 where the shaking, vibration and movement of the particles during the static transfer of the mixed sample will allow the sample to separate, i.e., heavier matter will fall to the bottom of the sample and the lighter matter will stay at the top. Thus, by transferring the sample while mixing, the sample is not allowed to settle and then be physically transferred to the collection cup 114. Therefore, the uniform mixture of the sample is maintained.

Those skilled in the art can now appreciate from the foregoing description that the broad teachings of the present invention can be implemented in a variety of forms. Therefore, while this invention has been described in connection with particular examples thereof, the true scope of the invention should not be so limited since other modifications will become apparent to the skilled practitioner upon a study of the drawings, specification and following claims.

What is claimed is:

1. An agricultural sample grinding system, said system comprising:
   a grinder unit for grinding and uniformly mixing an agricultural sample; and
   a collection chamber connected to a transfer spout extending from a side of the grinder unit, the collection chamber for collecting the ground and uniformly mixed agricultural sample dispensed from the grinder unit via the transfer spout;
   wherein the grinder unit includes a grinding chamber and a routing channel formed in the grinding chamber, the grinding chamber configured to allow centrifugal movement of the ground and uniformly mixed agricultural sample around the grinding chamber, and the routing channel configured to guide the ground and uniformly mixed agricultural sample around the grinding chamber to the transfer spout such that the uniform mixture of the ground agricultural sample is maintained as it is expelled from the grinding chamber through the transfer spout.

2. The system of claim 1, wherein the agricultural sample comprises at least one seed.

3. The system of claim 1, wherein the agricultural sample comprises plant tissue.

4. The system of claim 1, further comprising a sample receptacle, and wherein the collection chamber defines an opening configured to receive at least part of the sample receptacle into the collection chamber for collecting and retaining at least part of the ground and uniformly mixed sample.

5. The system of claim 4, wherein the sample receptacle comprises a collection cup insertable through the opening of the collection chamber.

6. The system of claim 4, wherein the sample receptacle comprises a collection tube.

7. The system of claim 1, wherein the collection chamber comprises a vacuum port through a side of the collection chamber for connecting a vacuum to remove excess ground sample from the collection chamber.

8. The system of claim 1, wherein the grinder unit comprises a bottom half and a top half, the bottom half including a bottom half of the grinding chamber and a grinding blade, and the top half including a top half of the grinding chamber.

9. The system of claim 8, wherein a surface of the grinding chamber is finished to provide a hard smooth surface adapted for easy removal of excess ground sample.

10. The system of claim 8, wherein the grinder unit further comprises an automatic transfer control assembly for transferring the ground and uniformly mixed sample from the grinding chamber to the collection chamber.

11. The system of claim 10, wherein the automatic transfer control system comprises:
- an outflow port in communication with the routine channel and extending from the bottom half of the grinding chamber through a side of the bottom half of the grinder unit;
- a flow control gate cooperative with the side of the bottom half of the grinder unit to control dispensing of the ground and uniformly mixed sample from the routing channel of the grinding chamber, the flow control gate including an aperture alignable with the outflow port by manipulation of the flow control gate; and
- the transfer spout connected to the side of the bottom half of the grinder unit such that an internal bore of the transfer spout aligns with the outflow port with the flow control gate positioned therebetween.

12. The system of claim 11, wherein the grinding blade is rotationally mounted within the bottom half of the grinding chamber, the blade for grinding and uniformly mixing the agricultural sample, and for creating a centrifugal force exerted by the spinning ground and uniformly mixed sample that is used to move the ground and uniformly mixed sample around the grinding chamber through the routing channel and to dispense the ground and uniformly mixed sample through the transfer spout into the collection chamber.

13. The system of claim 12, wherein an interior surface of the bottom half of the grinding chamber is contoured to provide a maximum amount of the ground and uniformly mixed sample dispensed from the grinding chamber.

14. An agricultural sample grinding system, said system comprising:
- a grinder unit including a grinding chamber for grinding and mixing an agricultural sample;
- a collection chamber connected to the grinder unit for collecting the ground and mixed agricultural sample dispensed from the grinding chamber of the grinder unit; and
- an automatic transfer control assembly for transferring the ground and mixed sample from the grinding chamber to the collection chamber, the automatic transfer control assembly comprising:
  - an outflow port in communication with the grinding chamber for receiving the ground and mixed agricultural sample from the grinding chamber;
  - a transfer spout positioned between the outflow port and the collection chamber for directing the ground and mixed agricultural sample between the outflow port and the collection chamber; and
  - a flow control gate positioned between the outflow port and the transfer spout for controlling movement of the ground and mixed agricultural sample between the outflow port and the collection chamber, the flow control gate moveable between at least a first position in which the flow control gate allows the ground and mixed agricultural sample to move between the outflow port and the collection chamber and at least a second position in which the flow control gate inhibits the ground and mixed agricultural sample from moving between the outflow port and the collection chamber;
  - wherein the grinder chamber and the automatic transfer control assembly are structured to maintain homogeneity of the ground and mixed sample as the sample is transferred from the grinder unit to the collection chamber.

15. The system of claim 14, wherein the agricultural sample comprises at least one seed.

16. The system of claim 14, wherein the agricultural sample comprises plant tissue.

17. The system of claim 14, further comprising a sample receptacle, and wherein the collection chamber defines an opening configured to receive at least part of the sample receptacle into the collection chamber for collecting and retaining at least part of the ground and mixed sample.

18. The system of claim 17, wherein the sample receptacle comprises one of a collection cup and a collection tube.

19. The system of claim 14, wherein the collection chamber comprises a vacuum port through a side of the collection chamber for connecting a vacuum to remove excess ground sample from the collection chamber.

20. The system of claim 14, wherein the grinder unit comprises a bottom half and a top half, the bottom half including a bottom half of the grinding chamber and a grinding blade, and the top half including a top half of the grinding chamber.

21. The system of claim 20, wherein a surface of the grinding chamber is finished to provide a hard smooth surface adapted for easy removal of excess ground sample.

22. The system of claim 14, further comprising a grinding blade rotationally mounted within the bottom half of the grinding chamber, the blade for grinding and mixing the agricultural sample, and for creating a centrifugal force exerted by the spinning ground and mixed sample that is used to move the around and mixed sample around the grinding chamber and to dispense the ground and mixed sample through the transfer spout into the collection chamber.

23. The system of claim 22, wherein an interior surface of the bottom half of the grinding chamber is contoured to maximize the amount of the ground and mixed sample dispensed from the grinding chamber.

24. The system of claim 22 further comprising a control unit communicatively coupled to grinder unit for controlling at least one of a speed at which the blade rotates and a length of time the blade grinds and mixes the sample.

25. The system of claim 14, wherein the grinding chamber includes a routing channel formed therein, the grinding chamber configured to allow centrifugal movement of the ground and mixed agricultural sample around the grinding chamber, and the routing channel configured to guide the ground and mixed agricultural sample around the grinding chamber to the transfer spout.

* * * * *